United States Patent [19]

Rapoport et al.

[11] Patent Number: 5,602,264

[45] Date of Patent: Feb. 11, 1997

[54] HIGHLY REACTIVE, WATER SOLUBLE CARBODIIMIDES, INTERMEDIATES AND DERIVATIVES THEREOF

[75] Inventors: Henry Rapoport, Berkeley, Calif.; Frank S. Gibson, Syracuse, N.Y.

[73] Assignee: The Regents of the University of California, Oakland, Calif.

[21] Appl. No.: 345,514

[22] Filed: Nov. 28, 1994

[51] Int. Cl.$^6$ .................. C07D 317/26; C07D 317/28
[52] U.S. Cl. ............................................. 549/448
[58] Field of Search ............................................. 549/448

[56] References Cited

U.S. PATENT DOCUMENTS

| 4,517,290 | 5/1985 | Iwasa et al. .................. 435/7 |
| 5,011,861 | 4/1991 | Coull et al. .................. 521/53 |

OTHER PUBLICATIONS

Gibson et al, "J. Org. Chem.", vol. 59 (24), pp. 7503–7507, 1994.
Chevallet et al., "Facile Synthesis of Tert–Butyl Ester of N–Protected Amino Acids with Tert–Butyl Bromide," *Tetrahedron Letters*, 34, No. 46, pp. 7409–7412 (1993).
Keller et al., "Copper(I) Chloride," Chapt. 1:1, pp. 1–4 in *Inorganic Syntheses*, 2, Ed. by Fernelius, New York: McGraw-Hill Book Company, Inc., (1946).
Miyazawa et al., "Effect of Copper(II) Chloride on Suppression of Racemization in Peptide Synthesis by the Carbodiimide Method," *Int. J. Peptide Protein Res.*, 39, pp. 237–244 (1992).
Miyazawa et al., "Simultaneous Use of 1–Hydroxybenzotriazole and Copper(II) Chloride as Additives for Racemization–Free and Efficient Peptide Synthesis by the Carbodiimide Method", *Int. J. Peptide Protein Res.*, 39, pp. 308–314 (1992).
Nestor, Jr. et al., "Potent, Long–Acting Luteinizing Hormone–Releasing Hormone Antagonists Containing New Synthetic Amino Acids: N,N'–Dialkyl–D–Homoarginies," *J. Med. Chem.*, 31, pp. 65–72 (1988).
Ponnusamy et al., "A Novel Method for the Rapid, Non–Aqueous t–Butoxycarbonylation of Some $^{17}$O–Labeled Amino Acids and $^{17}$O–M.M.R. Parameters of the Products, "*Synthesis*, No. 1, pp. 48–49 (Jan. 1986).
Sakaki et al., "Synthesis of 1,3–Dioxin–4–ones and Their Use in Synthesis . . . ," *Chem. Pharm. Bull.*, 37, No. 11, pp. 2952–2960 (1989).

*Primary Examiner*—Ba K. Trinh
*Attorney, Agent, or Firm*—Majestic, Parsons, Siebert & Hsue

[57] ABSTRACT

Novel water soluble carbodiimides, and intermediates or derivatives thereof, such as isoureas or isothioureas, are described. A particularly preferred embodiment is bis[4-(2,2-dimethyl-1,3-dioxolyl)methyl] carbodiimide (BDDC), which can be synthesized efficiently from 1,2-isopropylideneglycerol (solketal). The isoureas are effective esterifying agents. The corresponding N-protected amino acid tert-butyl, benzyl, isopropyl, ethyl, and methyl esters can be synthesized in high yield under neutral conditions, with no urea residue after simply washing with aqueous acid. Amino acid couplings utilizing carbodiimide embodiments give peptides in good yield, free of carbodiimide by-products, after washing with dilute acid, while racemization-free peptides are also obtained.

7 Claims, 2 Drawing Sheets

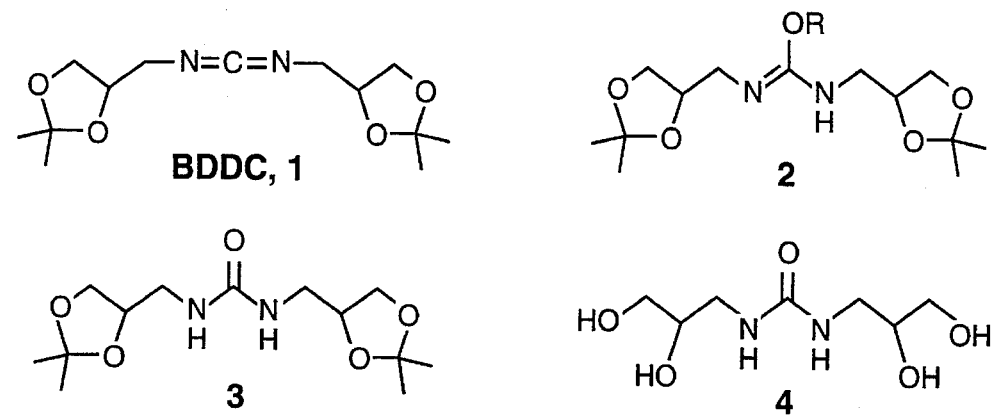
FIG._1
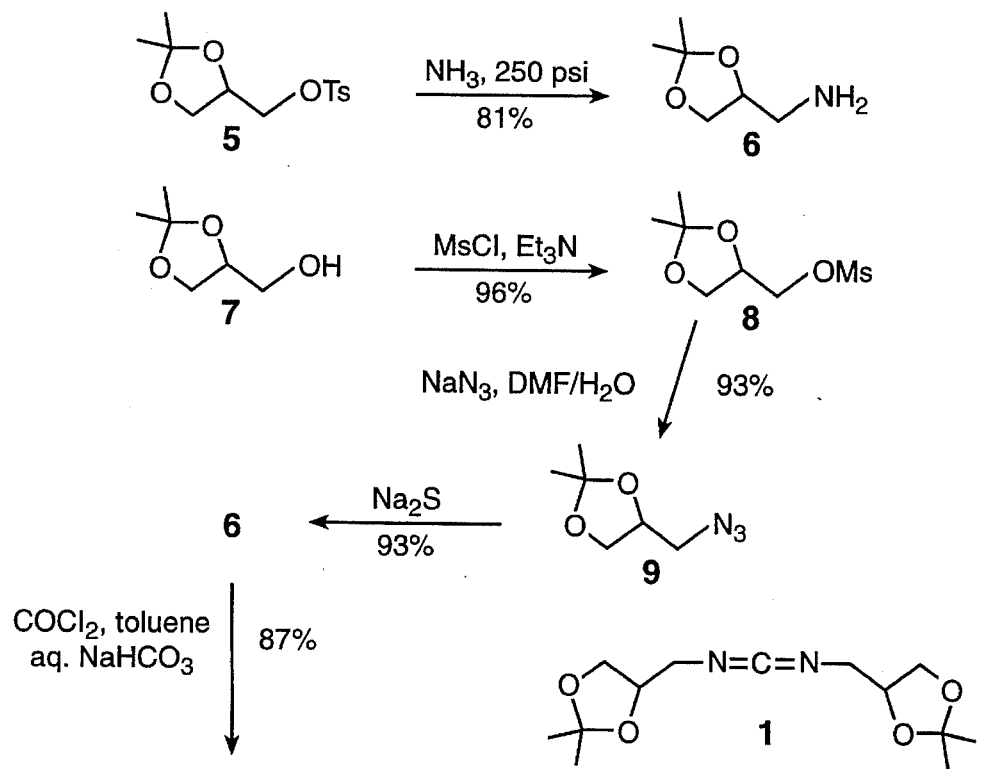
FIG._2

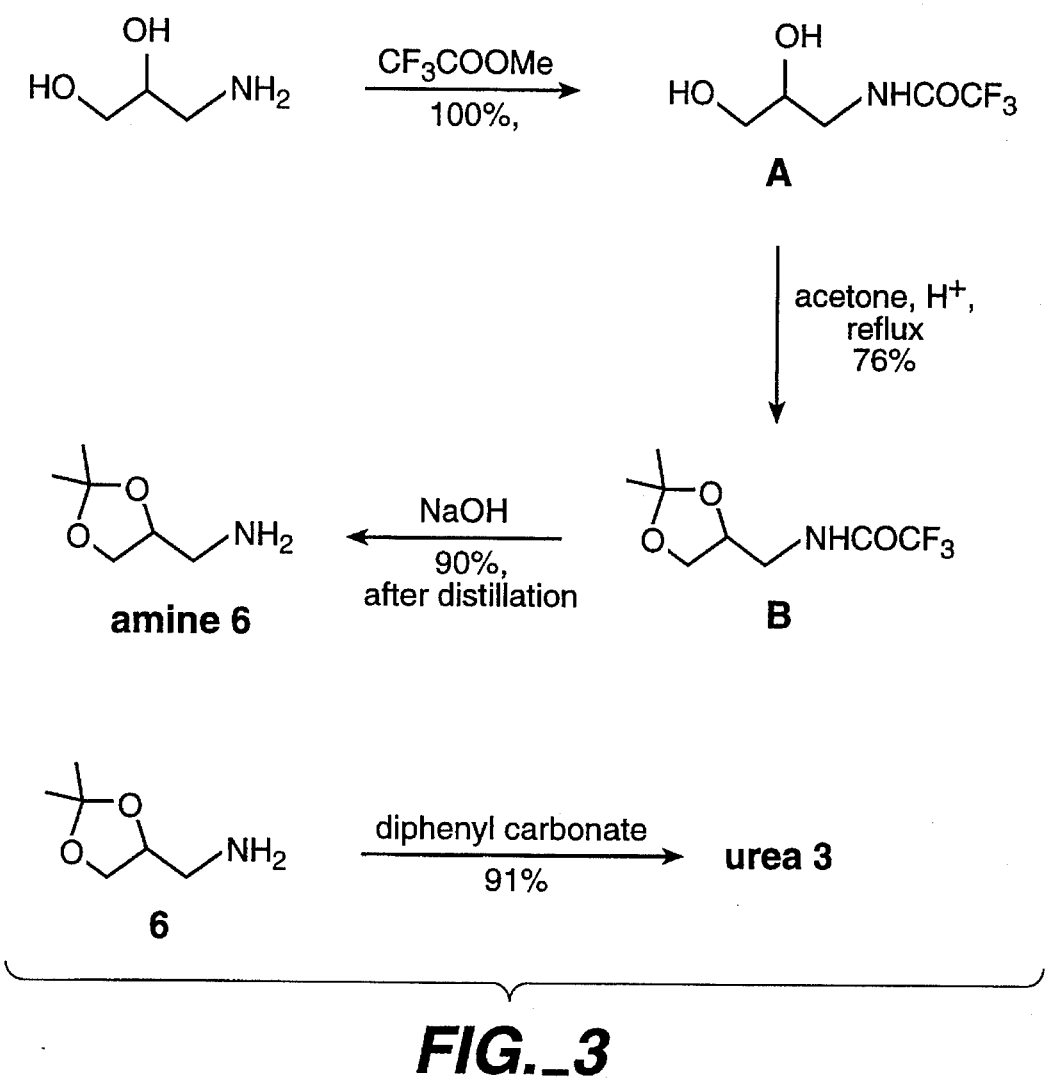
FIG._3

HIGHLY REACTIVE, WATER SOLUBLE CARBODIIMIDES, INTERMEDIATES AND DERIVATIVES THEREOF

FIELD OF THE INVENTION

The present invention relates generally to carbodiimides, and more particularly relates to highly reactive carbodiimides that are water soluble and are useful in a wide variety of organic syntheses, such as in peptide coupling.

BACKGROUND OF THE INVENTION

Carbodiimides are important reagents in synthetic chemistry and are employed in a wide variety of transformations, in which they generally function as dehydrating agents. Carbodiimides such as dicyclohexylcarbodiimide (DCC), diisopropylcarbodiimide (DIC), and 1-(3-dimethylaminopropyl)-3-ethylcarbodiimide hydrochloride (EDC) are used primarily as peptide coupling reagents, and are employed less frequently for direct O-acylations.

A major problem in the use of carbodiimides such as DCC or DIC has been the frequently encountered difficulty of separating the desired reaction product from the neutral urea formed as a result of the dehydration and still retained with the organic material. EDC and other "water soluble" carbodiimides have addressed this issue, as the resulting urea by-products formed from the dehydration reaction are basic and can be easily removed with a dilute acid wash.

For example, in connection with membranes for solid phase protein sequencing discussed by U.S. Pat. No. 5,011,861, issued Apr. 30, 1991, when nucleophiles having both amino and thiol functions are contacted with a reagent such as PVDF, the thiol functions react to bind the nucleophile to the membrane surface, thereby allowing the amino functions to remain free for the coupling of the peptide or protein to the membrane. This coupling can be achieved by reacting carboxyl groups within the peptide or protein with the amino groups using carbodiimides (noted as being preferably those which are water-soluble). Thus, these carbodiimides reagents are capable of effecting a dehydrative condensation of the reactive amino group of the peptide with the reactive carboxyl group of the mating material in an aqueous solvent.

In addition to protein sequencing, other applications pertaining to protein coupling (formation of peptide bonds) include preparations of peptide-enzyme conjugates (e.g. U.S. Pat. No. 4,517,290, issued May 14, 1985).

Further, carbodiimides have found applications as sources of isoureas for esterification, typically to introduce tert-butyl esters. Many methods have been reported for the synthesis of tert-butyl esters, a number of which rely on strong acids, bases, or expensive and toxic reagents. For example, N,N'-diisopropyl-O-tert-butyl isourea has been the reagent of choice for the introduction of the tert-butyl ester into a variety of N-protected amino acids and derivatives. This reagent gives good yields of tert-butyl esters, but has several drawbacks. The formation of isourea proceeds slowly and in only moderate yield, and requires CuCl to catalyze the conversion. The resulting reaction mixture must be washed, filtered, and distilled to obtain acceptably pure reagent. Removal of the residual N,N'-diisopropylurea formed in the esterification reaction from the target ester can be difficult and chromatography is often necessary.

However, the previously known water soluble carbodiimides typically bear charged or basic amino groups, and their corresponding isoureas are ineffective for esterifications which depend on initial protonation of the isourea moiety. In ester formation, carbodiimides such as DCC and DIC have been used infrequently as direct O-acylating agents, due in part to the formation of undesirable N-acylurea as well as the accompanying urea, which can further complicate purification.

Consequently, new carbodiimides that are highly reactive but which are easy (in their original form or their derivatized form after the reaction) to remove gently are still needed for applications in a variety of organic syntheses.

SUMMARY OF THE INVENTION

In one aspect of the present invention, novel carbodiimides having the structure illustrated by Structure I are provided,

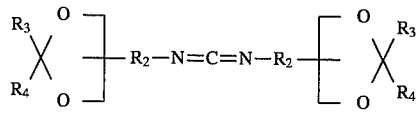

where $R_2$ is an alkylene having 1 to 5 carbons, and $R_3$ and $R_4$ are each H, an alkyl having 1 to 5 carbons, a cycloalkyl having 5–6 carbons, an aryl having 6 carbons or a heteroaryl having 3 to 5 carbons, and the heteroatom is one or more of N, O, or S. $R_3$ and $R_4$ can be the same or different.

The Structure I carbodiimide may be readily synthesized, typically through a urea or thiourea intermediate having the structure illustrated by Structure III,

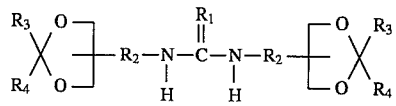

where $R_1$ is O or S, $R_2$ is an alkylene having 1 to 5 carbons, and $R_3$ and $R_4$ are each H, an alkyl having 1 to 5 carbons, a cycloalkyl having 5 to 6 carbons, an aryl having 6 carbons, or a heteroaryl having 3 to 5 carbons and the heteroatom is one or more of N, O, or S.

Among the applications of the Structure I embodiments are use as an isourea derivative to deliver an alkyl group, such as is provided through use of the compound illustrated by Structure II,

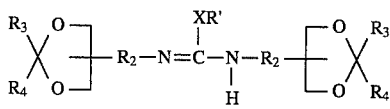

where R' is an alkyl having 1 to 12 carbons, a cycloalkyl having 3 to 6 carbons, or a heterocycloalkyl having 3 to 6 carbons, where the heteroatom is N, O, or S, X is O or S, $R_2$ is an alkyl having 1 to 5 carbons, and $R_3$ and $R_4$ are each selected from the group consisting of H, an alkyl having 1 to 5 carbons, a cycloalkyl having 5 or 6 carbons, an aryl having 6 carbons, and a heteroaryl having 3 to 5 carbons and the heteroatom is one or more of N, O, or S, and wherein $R_3$ and $R_4$ can be the same or different.

The novel carbodiimides, intermediates and derivatives of this invention, are useful in organic synthesis applications where high yield, racemization-free esterifications and readily removed by-products (or excess, unreacted reagents) are desired. The novel carbodiimides of this invention are uniquely hydrophilic, which allows for easy removal from organic reaction media with simple dilute acid extraction, thus leaving the desired products free of carbodiimide derived reaction by-products.

BRIEF DESCRIPTION OF THE DRAWINGS

FIG. 1 illustrates four embodiments of this invention where compound 1 is a carbodiimide, compound 2 is an isourea, compound 3 is an urea (and can alternatively be a thiourea) while compound 4 is a tetraol;

FIG. 2 illustrates one scheme for the synthesis of the carbodiimide embodiment 1; and FIG. 3 illustrates another, alternative synthesis.

DETAILED DESCRIPTION OF THE PREFERRED EMBODIMENTS

Novel carbodiimides of this invention have neutral alkyl substituents, form isoureas in good yield and high purity, are symmetrical (with respect to the —N=C=N— core), and give reaction residues, including the corresponding isourea and urea, that are readily removed from the organic product.

An important and broadly applicable use of isoureas of this invention is the introduction of a protecting group, such as tert-butyl ester. The tert-butyl ester is a versatile synthetic protecting group, easily removed under non-racemizing acidic conditions and orthogonal to many N- and O- protecting groups. The substantial steric bulk of a tert-butyl ester also contributes as a temporary stereo-directing group.

With reference to FIG. 1, one preferred new carbodiimide embodiment of this invention is bis[4-(2,2-dimethyl-1,3-dioxoly)methyl]carbodiimide (BDDC, 1). We have found 1 to be a superior reagent for the formation of isoureas, especially tert-butyl isourea derivative 2 (R=BU$^t$), as well as being an effective peptide coupling reagent and general dehydration agent.

Embodiments of this invention include the isoureas 2 and corresponding urea 3, formed from 1, which are efficiently washed from organic mixtures with dilute acids such as 0.1N HCl or phosphoric acid, since they have significant distribution into the aqueous phase from an organic solvent. Once in the water phase, the propanediol isopropylidene ketal side chains rapidly hydrolyze to reveal the very hydrophilic tetraol 4 and make the extraction total. The neutrality of the propanediol isopropylidine ketal side chains allows for enhanced organic solubility, ease of isourea formation, and use.

Broadly, carbodiimide embodiments of this invention have the below illustrated Structure I.

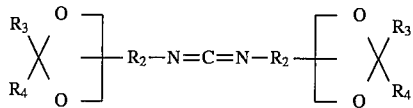

where $R_2$ is an alkylene having 1 to 5 carbons, and $R_3$ and $R_4$ are each H, an alkyl having 1 to 5 carbons, a cycloalkyl having 5–6 carbons, an aryl having 6 carbons or a heteroaryl having 3 to 5 carbons, and the heteroatom is one or more of N, O, or S. $R_3$ and $R_4$ can be the same or different. Compounds of the invention generally having Structure I can be either in a D- or L-configuration, rather than a racemic mixture, although racemic mixtures typically are less expensive and serve their desired functions well.

The Structure I embodiments are useful as sources of isoureas for esterification, such as in applications where one wishes to introduce a blocking group such as tert-butyl esters. Isourea embodiments of the invention are generally illustrated by Structure II.

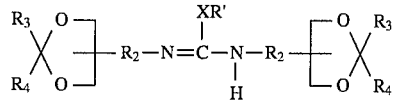

where R' is an alkyl having 1 to 12 carbons, a cycloalkyl having 3 to 6 carbons, or a heterocycloalkyl having 3 to 6 carbons, where the heteroatom is N, O, or S, X is O or S, $R_2$ is an alkyl having 1 to 5 carbons, and $R_3$ and $R_4$ are each selected from the group consisting of H, an alkyl having 1 to 5 carbons, a cycloalkyl having 5 or 6 carbons, an aryl having 6 carbons, and a heteroaryl having 3 to 5 carbons and the heteroatom is one or more of N, O, or S, and wherein $R_3$ and $R_4$ can be the same or different.

A key intermediate in practicing the invention is the thiourea or urea derivative, generally illustrated as Structure III.

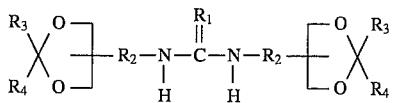

where $R_1$ is O or S, $R_2$ is an alkylene having 1 to 5 carbons, and $R_3$ and $R_4$ are each H, an alkyl having 1 to 5 carbons, a cycloalkyl having 5 to 6 carbons, an aryl having 6 carbons, or a heteroaryl having 3 to 5 carbons and the heteroatom is one or more of N, O, or S.

Aspects of this invention will be illustrated particularly through using the preferred carbodiimide embodiment BDDC, 1, having the general Structure I. The usefulness of 1 as a source of isoureas for esterification, primarily as a method to introduce tert-butyl esters, is illustrated as follows.

Reaction of 1 at room temperature with 400 mol % of tert-butanol and 1–2 mol % of freshly prepared CuCl gave a quantitative yield of analytically pure tert-butyl isourea 2 (R=Bu$^t$) in less than 1 h. The reaction was monitored using IR by following the disappearance of the carbodiimide absorption at 2130 cm$^{-1}$ and the appearance of the isourea absorbance at 1660 cm$^{-1}$. No purification other than evaporation of the excess tert-butanol was necessary to obtain the pure material. Isourea 2 (R=BU$^t$) was then stirred with N-CBZ-Ala (10) in several solvents under a variety of reaction conditions to determine the most effective conditions for tert-butyl ester formation. In general, all the solvents examined gave reasonable yields of N-CBZ-Ala-OBu$^t$ (15), but warm toluene, overnight, produced the best results. Several other N-BOC protected amino acids were treated with 2 (R=Bu$^t$) and gave good yields of tert-butyl esters under similar conditions. In each example, the yields were comparable if not slightly superior to those obtained using DIC. Esterification of the racemization sensitive CBZ-Ala-Phe (11) with 2 (R=Bu$^t$) gave the tert-butyl ester 20, shown by HPLC analysis to be a single diastereomer. Esterification of 11 using $K_2CO_3$ and tert-butyl bromide in DMA (Chevallet et al., *Tetrahedron Lett.*, 34, p. 7409 (1993)) gave 20 with 2.5% racemization to the L,D diastereomer. Other isourea derivatives 2 (R=Bn, Pr$^i$, Et Me) of 1 were synthesized, with results identical to that of 2 (R=Bu$^t$). Each isourea was formed rapidly and quantitatively at room temperature with 1–2 mole % CuCl and only a slight excess of alcohol. The quality of the CuCl catalyst was important, as older samples gave slower reactions and were required in up to 5 mol %. Surprisingly, each isourea, including the Bu$^t$, could be produced quantitatively without the use of catalytic CuCl, although heating and longer reaction times were required. In the case of DIC, no isourea was obtained without catalytic CuCl. All our results indicated that the presence or absence of the CuCl had no effect on esterifications.

The removability of isoureas 2 and urea 3 was examined during isolation of the esterification products. Dilution with EtOAc, two washes with 1N HCl followed by one with aqueous bicarbonate gave pure product ester after evaporation of the organic solvent, as judged by NMR, tlc, and mass balance. Both NMR and tlc showed the absence of any 2 or 3 in the organic phase. A more precise measurement of the acid extractability of 1 and its derivatives 2 and 3 was made by dissolving a measured quantity of each in an organic solvent, (ethyl acetate, dichloromethane, or toluene) extracting with aqueous acid (HCl or $H_3PO_4$) and weighing the residue left after evaporation of the organic solvent. Each of the compounds tested was removed to the extend of >99% after two acid washes, regardless of the organic solvent. Acid no more than 0.1M was sufficient to remove most reagent residues. Even water (pH 7) removed greater than 80% of residual mass after only two washes; 1 and its derivatives clearly possessed the necessary solubility properties.

Having shown the removability of 1 and its derivatives from organic solvents, we next demonstrate its effectiveness as a peptide coupling reagent and general dehydrating agent. Coupling CBZ-Ala (10) and Phe-OMe.HCl in THF with HOBT and 1 afforded CBZ-Ala-Phe-OMe (21) in 84% yield. Using DMF as the solvent, the yield increased to 93%. The more hindered coupling of BOC-Ile (26) and Phe-OMe.HCl with HOBT and 1 produced yields of 82% and 85% of BOC-Ile-Phe-OMe (26) in THF and DMF, respectively. In all cases there was no racemization, as would be expected from N-carbamate-protected amino acids. The 1/HOBT mediated C-terminus coupling of CBZ-Ala-Phe (11) with Gly-OBn.TsOH in DMF produced CBZ-Ala-Phe-Gly-OBn (27) in which the Phe was racemized to the extent of 0.68% after 4 h and 1.3% after 20 h, consistent with similar experiments using DCC and EDC. The same coupling carried out in the presence of 50 mol % of anhydrous $CuCl_2$ gave racemization-free 27, even after reactions were allowed to proceed for 20 h at room temperature. These results were also in agreement with literature data. (Miyazawa et al., *Int. J. Peptide & Protein Res.*, 39, p. 237 (1992); Miyazawa et al., *Int. J. Peptide & Protein Res.*, 39, p. 308 (1992).) In each case, all residual 1 and urea by-products 3 were easily removed from the reaction mixtures with a simple acid wash.

The above described experimental results are summarized by Tables 1 and 2.

TABLE 1

Ester Formation Using BDDC Derived Isoureas 2

| Substrate | Conditions | 2,R | Ester Product | Yield |
|---|---|---|---|---|
| CBZ—Ala (10) | toluene 85° C., 20 h | Bu$^t$ | 15 | 94% |
| 10 | THF 45° C., 20 | Bn | 16 | 92% |
| 10 | THF reflux, 16 h | Pr$^i$ | 17 | 87% |
| 10 | DMF rt, 16 h | Et | 18 | 81% |
| 10 | DMF | Me | 19 | 93% |

TABLE 1-continued

Ester Formation Using BDDC Derived Isoureas 2

| Substrate | Conditions | 2,R | Ester Product | Yield |
|---|---|---|---|---|
| CBZ—Ala—Phe (11) | rt, 16 h toluene 85° C., 14 h | Bu$^t$ | 20 | 87%[a] |
| 11 | DMF rt, 20 h | Me | 21 | 82%[a] |
| bis-BOC—Orn (12) | toluene 80° C., 20 h | Bu$^t$ | 22 | 86% |
| bis-BOC—His (13) | toluene 80° C., 20 h | Bu$^t$ | 23 | 77% |
| BOC—Pro (14) | toluene 80° C., 20 h | Bu$^t$ | 24 | 90% |

[a]HPLC analysis of the product indicated less than 0.1% of the L, D diastereomer present.

TABLE 2

Peptide Coupling Using BDDC, 1[a]

| Substrate | Amine Salt | Solvent time h | Coupled Product | Yield (L,D)[b] % |
|---|---|---|---|---|
| CBZ—Ala (10) | Phe—OME.HCl | GHF 24 | 21 | 84 |
| 10 | Phe—OME.HCl | DMF 24 | 21 | 93 |
| BOC—Ile (25) | Phe—OME.HCl | THF 16 | 26 | 82 |
| 25 | Phe—OME.HCl | DMF 16 | 26 | 84 |
| CBX—Ala—Phe (11) | Gly—OBn.TsOH | DMF 4 | 27 | 81 (0.68) |
| 11 | Gly—OBn.TsOH | DMF 20 | 27 | 91 (1.3) |
| 11 | Gly—OBn.TsOH | DMF 4[c] | 27 | 71 (<0.1) |
| 11 | Gly—OBn.TsOH | DMF 20[c] | 27 | 78 (<0.1) |

[a]All reactions were conducted at rt using N-methylmorpholine and HOBT.
[b]The analytical limit for detection of L,D diastereomers is 0.1%
[c]With 50 mol % of anhydrous $CuCl_2$.

Finally, 1 was demonstrated to be a potential general dehydrating agent. Benzyl 3-hydroxy-butanoate was heated with 1 and 5 mol % of fresh CuCl. This produced benzyl crotonate in 83% yield.

Thus, we have prepared novel, readily synthesized carbodiimides, which are useful for racemization-free esterifications and peptide couplings and for dehydrations. The uniquely hydrophilic properties of these carbodiimides and their isourea derivatives allow for easy removal from organic reaction media with simple dilute acid extraction, leaving the desired products free of carbodiimide derived reaction by-products.

As will be readily understood by persons skilled in the art, the inventive embodiments include thioureas (Structure III) where $R_1$ is S. Thiourea embodiments can be prepared in a manner analogous to the Structure I compounds, but from thiophosgene rather than, for example, from phosgene.

One aspect of this invention is to use embodiments for coupling reactions, such as in the formation of peptide bonds between a first amino acid containing moiety and a second amino acid containing moiety. It will be readily understood that each of these amino acid containing moieties includes one or more amino acids. When there is more than one amino acid residue in a peptide residue, then they are normally linked by a peptide carbamoyl group, i.e. by —CONH—. Preferably a peptide residue consists of natural amino acid residues, but the unusual or unnatural amino acid residues can also be used. Unnatural amino acids to stabilize or to increase potency and prolong duration of action are illustrated, for example, by an article of Nestor et al., *J. of Med. Chem.*, 31(1), pp. 65–72 (1988). When there are amino acid residues in the unnatural configuration, then there preferably are only one or two such amino acid residues, especially only one, in the unnatural configuration. "Amino acid residue" as used herein also includes imino acid residues, such as proline and hydroxyproline.

Coupling reactions may be carried out with the aid of carboxyl group activating compounds such as inventive embodiments having Structure I, and with the α-amino group of the one amino acid moiety protected with a protecting group, such as an alkoxy-ω-oxoalkanoyl of 2–10 carbon atoms, alkoxycarbonyl of overall 2 to 10 carbon atoms, alkanoyl of overall 2 to 10 carbon atoms, cycloalkylcarbonyl of overall 4 to 8 carbon atoms, carbamoyl, alkylcarbamoyl, or dialkyl carbamoyl, a benzoyl, an alkylsulfonyl of overall 1 to 10 carbon atoms, especially alkoxycarbonyl of overall 4 to 8 carbon atoms, or alkanoyl of overall 2 to 6 carbon atoms. Cycloalkylcarbonyl preferably is of overall 4, 6, or 7 carbon atoms. Alkylsulfonyl preferably is of 3 to 6 carbon atoms, and preferably is branched. Examples are tert-butyloxycarbonyl (BOC), benzyl (BZL), p-methylbenzyl (MBZL), tert-amyloxycarbonyl (AOC), tosyl (TOS), o-bromobenzyloxycarbonyl (BrZ), cyclohexyl (OHEX), or dichlorobenzyl (BZLCl$_2$). As an alternative to adding each amino acid separately to the reaction, some may be coupled prior to addition of the solid phase reactor.

Other aspects of this invention will now be further illustrated by reference in the following experimental description.

EXPERIMENTAL

All moisture sensitive reactions were carried out in oven-dried glassware under a nitrogen atmosphere. Toluene, tert-butanol, DMF, triethylamine, and dichloromethane were distilled from CaH$_2$; THF was distilled from sodium benzophenone ketyl; NMM was distilled prior to use, and stored under nitrogen. Anhydrous CuCl was prepared by the method of Keller et al., *Inorg. Synths.*, 2, p. 1 (1946). Anhydrous CuCl$_2$ was prepared by heating CuCl$_2$·2H$_2$O at 100° C. and 0.1 mm Hg for 24 hours. N-BOC and N-CBZ protecting groups were introduced by the method of Ponnasamy et al., *Synthesis*, 48 (1986). IR spectra were recorded as thin films with absorptions reported in cm$^{-1}$. $^1$H NMR spectra were recorded at 300 MHz in CDCl$_3$ using TMS as an internal reference unless otherwise noted. $^{13}$C NMR spectra were recorded at 75 MHz. All chemical shifts (δ) are reported in ppm and coupling constants are in hertz. Melting points are uncorrected. Final organic extracts were dried over Na$_2$SO$_4$.

Solketal Mesylate (8). Solketal (7, 250 g, 1.8 mol) and triethylamine (300 mL, 217 g, 120 mol %) were dissolved in 750 mL of dichloromethane and cooled to 0° C. Mesyl chloride (163 mL, 241 g, 115 mol %) was added over 1.5 h to the vigorously stirred solution. The reaction mixture was allowed to stir for an additional 15 h at room temperature after addition of mesyl chloride had been completed. The resulting slurry was washed with 2×200 mL portions of saturated aqueous sodium bicarbonate, followed by 3×200 mL portions of water. The organic layer was dried, filtered, and evaporated to an orange oil mesylate 8 (379 g, 96%), which was converted to azide 9 without further purification:

$^1$H NMR δ 4.30–4.28 (m, 1H), 4.12 (d, 2H, J=5.5), 4.01 (dd, 1H, J=6.5, 8.8), 3.76 (dd, 1H, J=5.7, 8.9), 2.98 (s, 3H), 1.35 (s, 3H), 1.27 (s, 3H). Anal. Calcd for C$_7$H$_{14}$O$_5$S: C, 40.0; H, 6.7. Found: C, 39.7; H, 6.7.

1-Azido-2,3-propanedial Isopropylidene Ketal (9). Mesylate 8 (376 g, 1.79 mol) was dissolved in 488 mL of DMF, followed by the addition of sodium azide (137 g, 120 mol %) in 440 mL of water and the resulting mixture was heated at 110° C. for 6 h; tlc analysis indicated complete consumption of 8. The reaction mixture was cooled to room temperature, 400 mL of saturated brine was added, the solution was extracted with 5×400 mL portions of ether, after which the extracts were combined and concentrated to approximately 1 L. The resulting organic solution was washed with 2×200 mL portions of water, dried over sodium sulfate and then evaporated to a yellow oil, azide 9 (325 g, 93%). This material was reduced to amine 6 without further purification: IR 2100; $^1$H NMR δ 4.21–4.15 (m, 1H), 3.97 (dd, 1H, J=6.4, 8.3), 3.70 (dd, 1H, J=6.0, 8.3), 3.32 (dd, 1H, J=4.6, 12.6), 3.21 (dd, 1H, J=5.6, 12.6), 1.40 (s, 3H), 1.31 (s, 3H).

1-Amino-2,3-Propanedial Isopropylidene Ketal (6). Azide 9 (192 g, 1.22 mol) was dissolved in 260 mL of CH$_3$OH. This solution was added to a solution of Na$_2$S(H$_2$O)$_9$ (367 g, 125 mol %) in 573 mL of H$_2$O and the two phase mixture was heated at 55° C. and stirred at that temperature for 24 h, leaving the mixture open to the atmosphere as N$_2$ evolved. The resulting homogeneous orange solution was saturated with NaCl and extracted with 7×200 mL portions of ether and the ether was dried, filtered, and evaporated to yield a viscous orange oil. This oil was distilled at reduced pressure (23°–28° C./1 Torr) to give 149 g of 6, 93% yield: IR 3400, 3300; $^1$H NMR δ 4.19–4.11 (m, 1H), 4.04 (dd, 1H, J=7.8, 6.5), 3.68 (dd, 1H, J=8.0, 6.4), 2.89–2.75 (m, 2H), 2.95 (s, 2H), 1.42 (s, 3H), 1.39 (s, 3H). Anal. Calcd for C$_6$H$_{13}$NO$_2$: C, 54.9; H, 10.0; N, 10.7. Found: C, 54.9; H, 9.7; N, 10.6.

N,N'-[4-(2,2-Dimethyl-1,3-dioxolyl)methyl]urea (3). A solution of amine 6 (149 g, 1.14 mol) in toluene (680 mL) was added to a solution of NaHCO$_3$ (192 g, 200 mol %) in 680 mL of H$_2$O. This two phase mixture was cooled to 0° C. and vigorously stirred as a freshly prepared solution of phosgene in toluene (231 mL, 2.46M solution, 50 mol %) was added dropwise over 2 h. The reaction mixture was allowed to stir at room temperature for an additional 16 h, the layers were separated, and the toluene was dried, filtered, and evaporated to give a white solid residue. The water layer was extracted with 3×300 mL portions of EtOAc, and the combined organics were dried and evaporated. The combined residual white solids were recrystallized from toluene/hexane to afford 142 g (87%) of urea 3; mp 108°–110° C.; IR 3350, 1640, 1570; $^1$H NMR δ 5.42 (br s, 2H), 4.26–4.19 (m, 2H), 4.08–4.00 (m, 2H), 3.71–3.62 (m, 2H), 3.56–3.41 (m, 2H), 3.29–3.18 (m, 2H), 1.41 (s, 6H), 1.38 (s, 6H). $^{13}$C NMR δ 158.6, 109.1, 75.3, 66.5, 42.6, 26.7, 25.2. Anal. Calcd for C$_{13}$H$_{24}$N$_2$O$_5$: C, 54.2; H, 8.4; N, 9.7. Found: C, 54.3; H, 8.7; N, 9.8.

Bis[4-(2,2-dimethyl-1,3-dioxolyl)methyl]carbodiimide (BBDC, 1). Triphenylphosphine (131 g, 110 mol %) was dissolved in 1.1 L of dry dichloromethane, and the resulting solution was cooled to 0° C. Bromine (25.7 mL, 80 g, 110 mol %) was added dropwise over 15 min, then triethylamine (157 mL, 114 g, 250 mol %) was added in one portion. Solid urea 3 (131 g, 0.45 mol) as added to the yellow suspension in small portions over 50 min. The resulting brown slurry was stirred at room temperature for an additional 3 h, the reaction mixture was diluted with 500 mL of hexane, the solids were filtered off and washed with ether, and the washings were combined with the filtrate. The combined organic phase was evaporated to a brown slurry which then was resuspended in fresh ether, again diluted with hexane, and the solids were filtered off and washed with ether. The procedure of evaporation, suspension, and filtration is repeated until no further solids precipitate (usually 4 cycles). The final viscous, clear brown oil, crude 1, was distilled bulb to bulb at reduced pressure to give pure 1 as a pale yellow oil, 107 g, 89% yield, which could be stored indefinitely at 0° C. under nitrogen: bp 115°–125° C., 0.3 mm; IR 2130; $^1$H NMR δ 4.15–4.10 (m, 2H), 3.98 (dd, 2H, J=6.2, 8.3), 3.68 (dd, 2H, J=5.8, 8.3), 3.31 (dd, 2H, J=5.6, 12.8), 3.24 (dd, 2H, J=5.8, 12.8), 1.39 (s, 6H), 1.29 (s, 6H); $^{13}$C NMR δ 139.6, 109.2, 74.8, 66.7, 48.6, 26.6, 25.1. Anal. Calcd for $C_{13}H_{22}N_2O_4$: C, 57.8; H, 8.2; N, 10.4. Found: C, 58.0; H, 8.1; N, 10.7.

General Procedure for One Synthesis of Isoureas 2. The synthesis of O-tert-butyl isourea 2 is representative. A mixture of 1 (5 g, 18.5 mmol) was stirred with 400 mol % of tert-butanol (5.5 g) and 2 mol % of freshly prepared CuCl (30 mg) at room temperature for 1 h. IR data indicated complete conversion of 1 to isourea 2 (disappearance of the carbodiimide absorption at 2130 and appearance of the isourea absorbance at 1665). Excess tert-butanol was removed under reduced pressure to leave a dark green semisolid residue, 6.41 g, 99%, which by NMR was a single product, 2, that was analytically pure; 2 was also produced without the use of CuCl but required heating at 70° C. for 24 h. The product 2 obtained was identical in yield and purity to 2 synthesized using CuCl: IR 3380, 1665; $^1$H NMR δ 5.12–5.03 (m, 1H), 4.36–2.95 (m, 10H), 1.50–1.24 (m, 21H). Anal. Calcd for $C_{17}H_{32}N_2O_5$: C, 59.3; H, 9.4; N, 8.1. Found: C, 59.2; H, 9.1; N, 8.1.

O-Benylisourea 2. Carboiimide 1, benzyl alcohol, and CuCl were treated according to the general procedure to give 2 (R=Bn) as a green oil; isourea 2 (R=Bn) could also be synthesized without using CuCl by heating 1 and benzyl alcohol (200 mol %) at 80° C. for 24 h; IR 3390, 3050, 1660; $^1$H NMR δ 7.40–7.23 (m, 5H), 5.14–5.10 (m, 1H), 4.71 (s, 2H), 4.45–3.11 (m, 10H), 1.57–1.20 (m, 12H). Anal. Calcd for $C_{20}H_{30}N_2O_5$: C, 63.5; H, 8.0; N, 7.4. Found: C, 63.7; H, 8.0; N, 7.1.

O-Isopropylisourea 2 was prepared from 1 with isopropanol and CuCl according to the general procedure to give 3 (R=Pr$^i$), as a dark green oil, which was used without further purification: IR 3380, 1660; $^1$H NMR δ 5.12–5.03 (m, 1H), 4.36–3.18 (m, 11H), 1.41 (s, 12H), 1.39–1.20 (m, 6H). Anal. Calcd for $C_{16}H_{30}N_2O_5$: C, 58.2; H, 9.1; N, 8.5. Found: C, 57.8; H, 8.9; N, 8.4.

O-Ethylisourea 2 was prepared from 1 with ethanol and CuCl according to the general procedure to give 2 (R=Et) quantitatively as a dark green oil; IR 3400, 1660; $^1$H NMR δ 5.13–5.10 (m, 1H), 4.30–4.20 (m, 2H), 4.11 (q, 2H, J=7.1), 4.10–4.00 (m, 2H), 3.81–3.80 (m, 1H), 3.77–3.68 (m, 1H), 3.40–3.11 (m, 4H), 1.43 (s, 6H), 1.39 (s, 6H), 1.24 (t, 3H, J=7.1). Anal. Calcd for $C_{15}H_{28}N_2O_5$: C, 56.9; H, 8.9; N, 8.9. Found: C, 56.6; H, 8.5; N, 8.7.

O-Methylisourea 2 was prepared from 1 with methanol and CuCl according to the general procedure to give 2 (R=Me) quantitatively as a dark green oil: IR 3400, 1665; $^1$H NMR δ 5.12–5.11 (m, 1H), 4.30–4.20 (m, 2H), 4.10–4.00 (m, 2H), 3.92 (s, 3H), 3.82–3.80 (m, 1H), 3.75–3.68 (m, 1H), 3.40–3.11 (m, 4H), 1.44 (s, 6H), 1.37 (s, 6H). Anal. Calcd for $C_{14}H_{26}N_2O_5$: C, 55.6; H, 8.7; N, 9.3. Found: C, 55.5; H, 8.5; N, 8.9.

General Isolation Procedure for Reactions using BDDC (1) or Isourea Derivatives 2. Upon completion of the reaction, the reaction mixture is diluted with an appropriate organic solvent, typically ether, EtOAc or dichloromethane. The organic layer is vigorously shaken for 2 min with two equal volumes of dilute aqueous acid (0.1–1.0N HCl being representative), followed by a single wash with saturated aqueous bicarbonate and finally water. The organic layer is dried, filtered, and evaporated to yield the desired product free of carbodiimide derivatives and by-products (urea).

General Procedure for tert-Butyl Ester Formation Using Isourea 2 (10) (R=Bu$^t$). The synthesis of CBZ-alanine tert-butyl ester (15) is representative. CBZ-Ala (223 mg, 1 mmol) was dissolved in 10 mL of dry toluene, 350–500 mol % of isourea 2 (R=Bu$^t$, 1.72 g) was added and the resulting solution was heated at 80°–85° C. for 20 h. The mixture was evaporated and isolation was effected according to the general procedure to give tert-butyl ester 15 (263 mg, 94%) as a clear, fairly mobile oils: $[\alpha]^{25}$D –23.8° (c 3.6, EtOH); IR 3340, 3060, 3030, 1725; $^1$H NMR δ 7.40–7.28 (m, 5H), 5.47 (d, 1H, J=6.7), 5.09 (s, 2H), 4.25 (t, 1H, J=7.3), 1.44 (s, 9H), 1.35 (d, 3H, J=7.1). Anal. Calcd for $C_{15}H_{21}NO_4$: C, 64.5; H, 7.6,; N, 5.0. Found: C, 64.2; H, 7.6; N, 5.0.

N,N'-bis-BOC-Ornithine tert-Butyl Ester (22) was synthesized from N,N'-bis-BOC-ornithine (12) according to the general procedure : yield, 86%; mp 80°–82° C.; $[\alpha]^{25}$D+ 11.3° (c 1.3, CHCl$_3$); $^1$H NMR δ 5.07 (br d, 1H, J=7.8), 4.63 (m, 1H), 4.16 (t, 1H, J=6.9), 3.14 (t, 2H, J=6.0), 1.82–150 (m, 4H), 1 .45 (s, 9H), 1.43 (s, 18H). Anal. Calcd for $C_{19}H_{36}N_2O_6$: C, 58.7; H, 9.3,; N, 7.2. Found: C, 58.7; H, 9.7; N, 7.2.

N-BOC-Proline tert-Butyl Ester (24) was synthesized from N-BOC-proline (14) according to the general procedure: yield, 90%; $[\alpha]^{25}$D –50.5° (c 3.4, CHCl$_3$); $^1$H NMR δ 4.12 (dd, 1H, J=3.4, 8.9), 3.60–3.39 (m, 2H), 2.29–2.16 (m, 1H), 2.00–1.80 (m, 3H), 1.51 (s, 9H), 1.46 (s, 9H). Anal. Calcd for $C_{14}H_{26}NO_4$: C, 61.7; H, 9.6,; N, 5.1. Found: C, 61.7; H, 9.6; N, 5.4.

N$^\alpha$,N$^\tau$-bis-BOC-Histidine tert-Butyl Ester (23) was synthesized from N$^\alpha$,N$^\tau$-bis-BOC-histidine (13) according to the general procedure: yield, 77%; mp 98° C.; $[\alpha]^{25}$D +17.8° (c 1.3, CHCl$_3$); IR 3880, 1750, 1710 cm$^{-1}$; $^1$H NMR δ 7.98 (d, 1H, J=0.8), 7.13 (s, 1H), 5.59 (br d, 1H, J=8.4), 4.43 (dd, 1H, J=2.9, 5.1), 3.00 (d, 2H, J=5.2). Anal. Calcd for $C_{20}H_{34}N_3O_6$: C, 58.2; H, 8.3,; N, 10.1. Found: C, 58.6; H, 8.2; N, 10.1.

CBZ-Ala-Phe-OBu$^t$ (20). CBZ-Ala-Phe ( 11, 0.1 g, 0.27 mmol) and isourea 2 (R=Bu$^t$, 0.56 g, 400 mol %) were combined in 5 mL of dry toluene and heated at 85° C. for 14 h. Isolation proceeded as in the general procedure to give 100 mg, 87% yield, of 20 as a white solid. HPLC analysis of the crude reaction mixture indicated <0.1% racemization: mp 119°–120° C.; $[\alpha]^{25}$D –15.0° (c 1.0, EtOH); $^1$H NMR δ 7.45–7.20 (m, 10 H), 6.42 (d, 1H, J=6.8), 5.27 (d, 1H, J=6.9), 5.10–5.06 (m, 2H), 4.72 (m, 1H), 4.24–4.22 (m, 1H), 3.08 (d, 2H, J=5.5), 1.40 (s, 9H), 1.34 (d, 3H, J=7). Anal. Calcd for $C_{24}H_{30}N_2O_5$: C, 67.6; H, 7.1,; N, 6.6. Found: C, 67.6; H, 7.1; N, 6.5.

CBZ-alanine Benzyl Ester (16). CBZ-Ala (10, 0.825 g, 0.0037 mol) was added to a solution of 2 (R=Bn, 2.8 g, 200 mol %) in 15 mL of THF. The reaction was heated at 45° C. for 20 h, after which the reaction was cooled, evaporated and following the general procedure gave 16 as a clear oil, 1.07 g, 92%: $[\alpha]^{25}$D –31.7° (c 1.1, EtOH); IR 3340, 3060, 3030, 1720; $^1$H NMR δ 7.45–7.28 (m, 10H), 5.43 (d, 1H, J=7), 5.15–5.08 (m, 4H), 4.43–4.40 (m, 1H), 1.38 (d, 3H, J=7.1). Anal. Calcd for $C_{18}H_{19}NO_4$: C, 69.0; H, 6.1,; N, 4.5. Found: C, 69.3; H, 6.2; N, 4.7.

CBZ-Ala-OPr$^i$ (17). CBZ-Ala (10, 0.46 g, 2 mmol) was dissolved in 15 mL of dry THF. Isopropyl isourea 2 (4 g, 600 mol %), was added and the reaction mixture was stirred for 16 h at reflux. Following the general procedure gave 0.475 g of 17, 87%, as a viscous oil yield; $[\alpha]^{25}D$ +1.3° (c 1.0, CHCl$_3$); IR 3340, 3060, 3030, 1720; $^1$H NMR δ 7.32–7.26 (m, 5H), 5.73 (d, 1H, J=7.5), 5.08 (s, 2H), 5.03–4.99 (m, 1H), 4.32–4.28 (m, 1H), 1.35 (d, 3H, J=7.2), 1.22 (d, 6H, J=6.0). Anal. Calcd for C$_{14}$H$_{19}$NO$_4$: C, 63.3; H, 7.2,; N, 5.3. Found: C, 63.2; H, 7.4; N, 5.6.

CBZ-Ala-OEt (18). CBZ-Ala (10, 0.165 g, 0.74 mmol) was added to 6 mL of dry DMF containing 1.12 g (500 mol %) of 2 (R=Et), and the mixture was stirred at room temperature for 16 h. Following the general procedure gave 0.151 g of 18, 81%, as an oil: $[\alpha]^{25}D$ –32.2° (c 1.0, MeOH) [Lit$^{14}$$[\alpha]^{25}D$ –32.0° (c 1.0, MeOH)]; IR 3350, 3060, 3030, 1720; $^1$H NMR δ 7.34–7.26 (m, 5H), 5.53 (d, 1H, J=7.2), 5.10 (s, 2H), 4.39 (t, 1H, J=7.3), 4.11 (q, 2H, J=7.1), 1.40 (d, 3H, J=7.2), 1.23 (t, 3H, J=7.3).

CBZ-Ala-OMe (19). CBZ-Ala (10, 0.165 g, 0.74 mmol) was added to 6 mL of dry DMF containing 1.1 g (500 mol %) of 2 (R=Me) and the reaction mixture was stirred at 16 h a t room temperature. Following the general procedure gave 0.163 g of 19, 93%, as an oil: $[\alpha]^{25}D$ –32.7° (c 1.3, MeOH) [Lit$^{14}$$[\alpha]^{25}D$ –33.0° (c 1.0, MeOH )]; IR 3340, 3060, 3030, 1720; $^1$H NMR δ 7.34–7.26 (m, 5H), 5.53 (d, 1H, J=5.9), 5.10 (s, 2H), 4.39 (t, 1H, J=7.3), 3.73 (s, 3H), 1.40 (d, 3H, J=7.2).

CBZ-Ala-Phe-OMe (21). Phenylalanine methyl ester hydrochloride (0.5 g, 2.3 mmol) was suspended in 10 mL of dry THF. Et$_3$n (0.35 mL, 2.5 mol) was added, after which both CBZ-Ala (10, 0.52 g, 100 mol %) and 1 (0.65 g, 104 mol %) were also added. The reaction mixture was stirred for 24 h at room temperature. Following the general procedure gave 21, 0.74 g, 84%, as a crystalline solid. An identical reaction using DMF as the solvent produced 21 in 93% yield: mp 97°–98° C.; $[\alpha]^{25}D$ –8.3° (c 0.3, EtOH); $^1$H NMR δ 7.42–7.15 (m, 10H), 6.40 (d, 1H, J=4), 5.24–5.21 (m, 1H), 5.10 (s, 2H), 4.88–4.84 (m, 1H), 4.24–4.21 (m, 1H), 3.78 (s, 3H), 3.16–3.13 (m, 2H), 1.38 (d, 3H, J=7). Anal. Calcd for C$_{21}$H$_{24}$N$_3$O$_5$: C, 65.5; H, 6.3,; N, 7.3. Found: C, 65.5; H, 6.3; N, 7.3. Compound 21 was also synthesized from the reaction of 11 and isourea 2 (R=M1) in DMF (82% yield) and was identical to material formed above.

CBZ-Ala-Phe-OH (11). To methyl ester 21 (1.64 g, 4.27 mmol) dissolved in 25 mL of THF and cooled to 0° C. was added LiOH.H$_2$O (0.25 g, 140 mol %) dissolved in 8 mL of water. The resulting solution was cooled to 0° C., added to the THF solution of 27, stirred at 0° C. for 0.5 h, then poured into 50 mL of saturated aqueous bicarbonate. The basic mixture was then extracted with 50 mL of ether which was discarded. The water layer was acidified with 1N HCl to pH 2 and extracted with 2×100 mL of ether. The organic extracts were combined, dried, and evaporated to give a thick white foam, which was crystallized from ether/hexane affording 1.53 g, 97% of 11 as a white powder; mp 126°–127° C.; $[\alpha]^{25}D$ +39.8° (c 2.1, CHCl$_3$); $^1$H NMR δ 11.5–11.1 (br s, 1H), 7.40–7.10 (m, 10H), 6.80 (d, 1H, J=5), 5.49 (d, 1H, J=4), 5.07 (s, 2H), 4.49–4.46 (m, 1H), 4.25–4.23 (m, 1H), 3.18 (dd, 1H, J=14, 5.5), 3.03 (dd, 1H, J=14, 6.5), 1.28 (d, 3H, J=7). Anal. Calcd for C$_{24}$H$_{22}$N$_3$O$_5$: C, 64.8; H, 6.0,; N, 7.6. Found: C, 64.8; H, 6.0; N, 7.4.

BOC-Ile-Phe-OMe (26). BOC-isoleuine (25, 0.5 g, 2.2 mmol), Phe-OMe.HCl, (0.464 g, 100 mol %), and HOBT (0.29 g, 100 mol %) were dissolved in 5 mL of dry THF to which 1 was added (0.58 g, 100 mol %) followed by 0.24 mL (100 mol % of N-methylmorpholine. The reaction mixture was stirred at room temperature for 16 h, then isolation followed the general procedure. The resulting solid was recrystallized from ether/hexane to give 26, 0.709 g, 82%. An identical reaction run in DMF gave 26 in 84% yield: mp 113°–114° C.; $[\alpha]^{25}D$ –27° (c 1.2, EtOH); $^1$H NMR δ 7.30–7.11 (m, 5H), 6.31 (d, 1H, J=6.8), 5.00 (d, 1H, J=8.2), 4.90–4.84 (m, 1H), 3.95–3.90 (m, 1H), 3.71 (s, 3H), 3.11 (t, 2H, J=5.3), 1.88–1.80 (m, 1H), 1.44 (s, 9H), 0.88 (d, 3H, J=6.8). Anal. Calcd for C$_{21}$H$_{32}$N$_2$O$_5$: C, 64.3; H, 8.2,; N, 7.1. Found: C, 64.6; H, 8.3; N, 7.0.

L,L-CBZ-Ala-Phe-Gly-OBn (27). Dipeptide 11 (0.2 g, 0.54 mmol), Gly-OBn.TsOH (0.364 g, 200 mol %), and HOBT (88 mg, 120 mol %) were combined in 4 mL of dry DMF. N-Methylmorpholine was added (0.18 mL, 300 mol %) followed by the addition of 0.16 g (110 mol %) of 1. The reaction mixture was allowed to stir for 5 h at room temperature, after which isolation followed the general procedure. The white solid residue obtained from evaporation of the organic extracts was completely dissolved into ethyl acetate, and the resulting solution was analyzed by normal phase HPLC (eluting with ethyl acetate/hexane, 1/1, at 1 mL/min), which indicated 0.68% of the L,D diastereomer of 27. Combined yield of products was 81%. In another experiment, a similar reaction was allowed to stir for 20 h, giving 1.3% of the L,D diastereomer as determined by HPLC. Combined yield of products was 90%. Recrystallization of the product mixture gave pure L,L-27 as a white solid: mp 160°–163° C.; $[\alpha]^{25}D$ –43.1° (c 0.7, CHCl$_3$); $^1$H NMR δ 7.48–7.21 (m, 15H), 6.65–6.58 (m, 2H), 5.27 (d, 1H, J=6.6), 5.13 (s, 2H), 5.08 (d, 1H, J=12), 5.00 (d, 1H, J=12), 4.74 (dd, 1H, J=7.2, 15), 4.16 (t, 1H, J=6.7), 4.13–3.87 (m, 2H), 3.20–3.00 (m, 2H), 1.23 (d, 3H, J=7). Anal. Calcd for C$_{28}$H$_{29}$N$_3$O$_6$: C, 67.3; H, 6.0,; N, 8.1. Found: C, 66.9; H, 6.0; N, 8.1.

Synthesis of 27 in the Presence of CuCl$_2$. Dipeptide 11 (0.2 g, 0.54 mmol), Gly-OBn.TsOH (0.364 g, 200 mol %), and HOBT (88 mg, 120 mol %) were combined in 4 mL of dry DMF. N-Methylmorpholine was added (0.18 mL, 300 mol %) followed by the addition of 0.16 g (110 mol %) of 1 and 90 mg of anhydrous CuCl$_2$ (50 mol %). The reaction mixture was allowed to stir for 4 h at room temperature, after which isolation followed the general procedure. The white solid obtained from the organic extracts was completely dissolved into ethyl acetate, and the resulting solution was analyzed by normal phase HPLC, which indicated <0.1% of the L,D diastereomer of 27. Combined yield of products was 71%. In another experiment, a similar reaction was allowed to stir for 20 h. This reaction gave <0.1% of the L,D diastereomer as determined by HPLC. Combined yield of products was 78%. Recrystallization of the product mixture gave pure 27, identical to 27 prepared above.

Benzyl Crotonate. Benzyl 3-hydroxyl-butanoate (Sakaki et al., *Chem. Pharm. Bull.*, 37, p. 2952 (1989)) (0.46 g, 2.4 mmol), CuCl (11 mg, 5 mol %), and 1 (0.7 g, 110 mol %) were combined in 20 mL of dry CH$_3$CN and heated to 60° C. for 16 h. The reaction mixture was cooled and evaporated, followed by isolation according to the general procedure to give benzyl crotonate (0.346 g, 83%) as a mobile oil: IR 3060, 3030, 1720; $^1$H NMR δ 7.40–7.20 (m, 5H), 7.00 (dq, 1H, J=15.5, 6.9), 5.86 (dq, 1H, J=16.0, 1.6), 5.18 (s, 2H), 1.83 (dd, 3H, J=1.7, 6.9).

The just described syntheses can alternatively be improved for syntheses of amine 6 and urea 3 in offering advantages in terms of time, cost, and safety, as is illustrated by FIG. 3. Thus, a particularly preferred synthesis of amine 6 begins with the very inexpensive 3-amino-propanediol and eliminates the use of MsCl, triethylamine, DMF, and NAN₃. The entire procedure can be carried out in one day, and requires no formal purifications until the final product.

The novel reagents of this invention are inexpensive, easily handled, and produce innocuous by-products which can be efficiently disposed of. Urea 3 can now be made without the use of phosgene, as diphenyl carbonate has shown to be an acceptable substitute. The yield of 3 is slightly improved, and the reaction is completed rapidly under simple experimental conditions.

Methyl Trifluoroacetate. Trifluoroacetate acid (2.48 mol, 283 g, 190 mL) and methanol (2.73 mol, 87.4 g, 110.5 mL) were combined with 8 mL of concentrated sulfuric acid in a 500 mL flask that was fitted with a distillation apparatus and large collecting flask. The reaction began to warm spontaneously, and gentle distillation was maintained with supplementary heating. All distillate from 38°–44° C. was collected. This two phase distillate was washed with one 150 mL portion of 10% aqueous bicarbonate and 100 mL of water. The resulting organic liquid was dried over $Na_2SO_4$, filtered and distilled (43° C.) to give 267 g (84%) of pure methyl trifluoroacetate.

3-N-Trifluoroacetylamino-1,2-propanediol (A). 3-Amino-1,3-propanediol (150 g, 1.65 mol) was dissolved in 150 mL of methanol, and the resulting solution was cooled to 0° C. in an ice bath. Methyl trifluoroacetate (211 g, 166 mL) was added rapidly dropwise to the vigorously stirred solution of amine. After the addition was complete, the cooling bath was removed and the reaction was allowed to stir at room temperature for 2 h. Removal of volatiles in vacuo left a viscous, clear oil, 311 g (101%) of A, that was used without further purification: IR 3320, 3100, 1710. Anal. Calcd for $C_5H_8F_3NO_3$: C, 32.09; H, 4.31; N, 7.48. Found: C, 32.28; H, 4.60; N, 7.41.

2,2-Dimethyl-4-(N-trifluoroacetylamino) methyldioxolane (B). Diol A (200 g, 1.07 mol) was dissolved in 400 ml (500 mol %) of acetone. Concentrated sulfuric acid (6 mL) was carefully added, and the solution was refluxed for 8 h. The reaction mixture was allowed to cool to room temperature, and solid sodium bicarbonate was added with stirring until the pH of the mixture was slightly basic. The solution was evaporated on a rotary evaporator to a mobile oil which was dissolved in 500 mL of ether and washed with 2×200 mL portions of saturated aqueous bicarbonate. The organic layer was dried with $Na_2SO_4$, filtered and evaporated to give 184 g (76%) of B: IR 3100, 1710; ¹H NMR δ 7.38 (br s, 1H), 4.35–4.25 (m, 1H), 4.10 (dd, 1H, J=6.5, 8.5), 3.68 (dd, 1H, J=5.9, 8.6), 3.65–3.55 (m, 1H), 3.45–3.35 (m, 1H), 1.41 (s, 3H), 1.38 (s, 3H). Anal. Calcd for $C_8H_{12}F_3NO_3$: C, 42.29; H, 5.33; N, 6.16. Found: C, 42.44; H, 5.36; N, 6.09.

Amine 6. Compound B (120 g, 0.53 mol) was dissolved in 50 ml of water and 50 mL of methanol. Sodium hydroxide (22.2 g, 105 mol %) was added in one portion, and the mixture was allowed to stir at room temperature for 1 h, at which time no starting material remained. Amine 6 was isolated from the reaction mixture after saturation with NaCl and vigorous extraction with ether. Yield after distillation is 90%, 62.5 g.

Urea 3. Amine 6 (50 g, 0.38 mol, slight excess) was added to diphenyl carbonate (0.185 mol, 40.3 g), and the resulting homogeneous reaction mixture was stirred at 50° C. until the indicated reaction was complete (3 h). Filtration through silica gel using ether as the eluent to remove phenol, then ethyl acetate to remove product gave urea 3 (48.5 g, 91%), as a thick oil, which crystallized on standing. The product was recrystallized from toluene/hexane, and was identical in all respects to the previously described material.

It is to be understood that while the invention has been described above in conjunction with preferred specific embodiments, the description and examples are intended to illustrate and not limit the scope of the invention, which is defined by the scope of the appended claims.

It is claimed:

1. A carbodiimide having the structure illustrated by Structure I

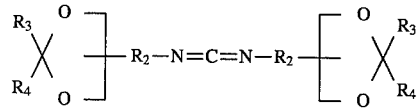

where $R_2$ is an alkylene having 1 to 5 carbons, and $R_3$ and $R_4$ are each H, an alkyl having 1 to 5 carbons, a cycloalkyl having 5–6 carbons, an aryl having 6 carbons or a heteroaryl having 3 to 5 carbons, and the heteroatom is one or more of N, O, or S, and wherein $R_3$ and $R_4$ can be the same or different.

2. A carbodiimide derivative having the structure illustrated by Structure II

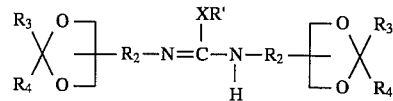

where R' is an alkyl having 1 to 12 carbons, a cycloalkyl having 3 to 6 carbons, or a heterocycloalkyl having 3 to 6 carbons, where the heteroatom is N, O, or S, X is O or S, R2 is an alkyl having 1 to 5 carbons, and $R_3$ and $R_4$ are each selected from the group consisting of H, an alkyl having 1 to 5 carbons, a cycloalkyl having 5 or 6 carbons, an aryl having 6 carbons, and a heteroaryl having 3 to 5 carbons and the heteroatom is one or more of N, O, or S, and wherein $R_3$ and $R_4$ can be the same or different.

3. A carbodiimide intermediate having the structure illustrated by Structure III

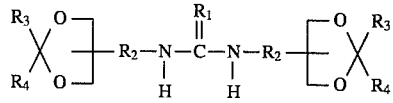

where $R_1$ is O or S, $R_2$ is an alkylene having 1 to 5 carbons, and $R_3$ and $R_4$ are each H, an alkyl having 1 to 5 carbons, a cycloalkyl having 5 to 6 carbons, an aryl having 6 carbons, or a heteroaryl having 3 to 5 carbons and the heteroatom is one or more of N, O, or S.

4. The compound as in claim 3 wherein $R_1$ is O.

5. The compound as in claim 2 wherein R' is a synthetic protecting group.

6. The compound as in claim 5 wherein R' is t-butyl, benzyl, ethyl, methyl, or isopropyl.

7. The compound as in claim 2 wherein R' is a stereo-directing group.

* * * * *

UNITED STATES PATENT AND TRADEMARK OFFICE
CERTIFICATE OF CORRECTION

PATENT NO. : 5,602,264
DATED : February 11, 1997
INVENTOR(S) : Rapoport et al.

It is certified that error appears in the above-indentified patent and that said Letters Patent is hereby corrected as shown below:

In Column 4, line 61:
replace "isourea derivatives 2($R$=Bn,$Pr^1$,Et Me) of 1 were synthesized," with:

--isourea derivatives 2($R$=Bn,$Pr^i$,Et,Me) of 1 were synthesized,--

In Column 10, line 39:
replace "the general procedure: yield, 77%; mp 98° C.;$[\alpha]^{25}_D$ +17.8°" with:

--the general procedure: yield, 77%; mp 97-98° C.;$[\alpha]^{25}_D$ +17.8° --

Signed and Sealed this

Thirteenth Day of January, 1998

Attest:

BRUCE LEHMAN

*Attesting Officer*     *Commissioner of Patents and Trademarks*